(12) United States Patent
Hütter et al.

(10) Patent No.: US 7,470,058 B2
(45) Date of Patent: Dec. 30, 2008

(54) METHOD AND DEVICE FOR A THERMOANALYTICAL MATERIAL ANALYSIS

(75) Inventors: Thomas Hütter, Niederrohrdorf (CH); Christoph Heitz, Elgg (CH); Jürgen Schawe, Bichelsee (CH)

(73) Assignee: Mettler-Toledo AG, Greifensee (CH)

( * ) Notice: Subject to any disclaimer, the term of this patent is extended or adjusted under 35 U.S.C. 154(b) by 157 days.

(21) Appl. No.: 10/563,773

(22) PCT Filed: Jul. 2, 2004

(86) PCT No.: PCT/EP2004/051335

§ 371 (c)(1),
(2), (4) Date: Jul. 13, 2006

(87) PCT Pub. No.: WO2005/003992

PCT Pub. Date: Jan. 13, 2005

(65) Prior Publication Data

US 2006/0256836 A1    Nov. 16, 2006

(30) Foreign Application Priority Data

Jul. 4, 2003    (EP)    ................... 03102015

(51) Int. Cl.
 *G01N 25/18*    (2006.01)
 *G01N 25/20*    (2006.01)
(52) U.S. Cl. .......................................... 374/43; 374/44
(58) Field of Classification Search ............. 374/10–13, 374/29–31, 33, 39, 43, E17.001, E17.006; 703/2
See application file for complete search history.

(56) References Cited

U.S. PATENT DOCUMENTS

| | | | |
|---|---|---|---|
| 4,812,051 A * | 3/1989 | Paulik et al. .................. 374/10 |
| 4,842,417 A | 6/1989 | Asbjornsen | |
| 5,148,365 A | 9/1992 | Dembo | |
| 5,346,306 A * | 9/1994 | Reading et al. ............... 374/10 |
| 5,453,940 A * | 9/1995 | Broomhead et al. ......... 702/109 |
| 6,092,017 A | 7/2000 | Ishida et al. | |
| 6,146,013 A * | 11/2000 | Huetter et al. ................ 374/46 |
| 6,428,203 B1 * | 8/2002 | Danley ....................... 374/10 |
| 6,497,509 B2 * | 12/2002 | Merzliakov et al. .......... 374/44 |
| 6,703,236 B2 * | 3/2004 | Atwood .................... 435/286.1 |
| 2002/0072112 A1 * | 6/2002 | Atwood et al. ........... 435/303.1 |
| 2004/0001524 A1 * | 1/2004 | Jorimann et al. .............. 374/10 |

FOREIGN PATENT DOCUMENTS

| | | |
|---|---|---|
| EP | 0 559 362 A1 | 9/1993 |
| JP | 10 123034 A | 5/1998 |

OTHER PUBLICATIONS

"Calibration of differential scanning calorimeters" by E. Gmelin and St.M. Sarge, 1995.*

* cited by examiner

*Primary Examiner*—Edward Lefkowitz
*Assistant Examiner*—Bret Adams
(74) *Attorney, Agent, or Firm*—Schwabe Williamson & Wyatt

(57) ABSTRACT

Substance analysis based upon observed reponse to excitation described herein. When a substance is subjected to an excitation and a response is observed, a relational evaluation is made based on the concept that the parameters of a mathematical model may be determined, which emulate the relationship between the excitation and the response, and that characteristic substance properties are subsequently determined/calculated from the time series of estimated values of the mathematical model.

27 Claims, 2 Drawing Sheets

METHOD AND DEVICE FOR A THERMOANALYTICAL MATERIAL ANALYSIS

BACKGROUND

Technical Field

Embodiments of the present invention relate generally to the field of the thermal analysis of substances; more particularly, to an apparatus and method where a substance is exposed to an excitation that causes an observable response, which is evaluated based on a time series of values of the excitation and measured values of the response.

By analyzing the response induced by methods of this kind in a substance as a result of an excitation acting on the substance, one can determine substance properties and substance parameters for the time interval of the analysis that is covered by the time series of measurements. The substance that is exposed to the excitation can be a pure substance, or it can also be a system or mixture of substances or materials.

In a dynamic thermal analysis, a substance is exposed to an excitation in the form of a given program of temperature vs. time, while the response observed in the analysis consists of the heat flow caused by the sample. This method is often performed as a differential method in which the test substance and a known reference substance are excited according to the temperature program, while the response that is analyzed in this case consists of the difference between the respective heat flows of the test sample and the reference sample. The thermomechanical analysis represents another known example. In this case, the response being analyzed consists of a change in length that occurs in a sample body formed of the test substance when the sample body is exposed to a given program of temperature vs. time.

In European Patent No. EP/0559362 issued to Reading, et al, a differential thermal analysis method of this kind, the temperature program that forms the excitation consists of a single excitation quantity in the form of a linearly rising ramp on which a periodic temperature modulation of a given frequency and a given amplitude is superimposed. The response obtained in the form of a difference between modulated heat flows as a single response quantity is evaluated based on splitting the response signal representing the difference between the heat flows into two signal components. One of the signal components is obtained by determining respective mean values for successive intervals consisting of single or multiple modulation periods, so that this signal component represents a monotonic part contained in the response signal. The other of the two signal components represents the alternating part contained in the response signal. The latter signal component oscillates with the given modulation frequency and is obtained by determining the difference between the measured response signal and is monotonic component. This concept of the excitation and the analysis of the response signal are based on using only one given, fixed modulation frequency, so that the excitation is only selectively effective for phenomena that belong to the same frequency or its harmonics.

This limitation to a single excitation frequency is avoided in anther known thermal analysis method, disclosed in U.S. Pat. No. 6,551,835 issued to Schawe, et al., wherein a stochastic excitation is proposed and the evaluation of the signal of the response quantity includes a correction analysis. However, to achieve a high level of accuracy with the correlation analysis method, the required length of time for the measurement increases.

SUMMARY

At least one embodiment of the present invention addresses the problem to provide a method that belongs to the kind that has been described herein and has the capability for an effective evaluation of the response with largely arbitrary forms of excitation, and also to present an apparatus that is operable to perform the method.

According to at least one embodiment of the invention, the foregoing task of providing a method is solved by using, for the evaluation of response signals, a mathematical model containing a finite number of parameters, which represents the relation between the excitation and the response. The parameters of the model are determined from the time series of excitation values and measurement values of the response as well as from the model itself. After the parameters have been determined in accordance with the various embodiments of the invention, the correlation between the excitation and the response is mirrored by the mathematical model. Thus, the responses of the substance to any kind of excitation can be determined even without exciting the substance itself. The evaluation of the responses of the model alone can be used to calculate characteristic properties of the substance. If the excitation is generated in the absence of a sample of the test substance in an apparatus configured to perform the method, the characteristic quantities of the apparatus instead of the characteristic quantities of the substance can be determined from the model. The excitation as well as the response can consist of more than one quantity. For the sake of simplicity, the principle of various embodiments of the invention is discussed herein primarily for a system with a single quantity.

In at least one embodiment of the present invention, at least a portion of the model is set up as time-invariant and linear. This embodiment acknowledges the fact that the correlation between the excitation and the response is, in many cases, at least approximately linear and time-invariant. As is generally known, in a linear, time-invariant model of this type, the correlation between the input signal representing the excitation and the output signal representing the response can be described by means of the impulse response function h(t). After the parameters of the model are determined, it is therefore possible to find the impulse response function directly. As is further known, the impulse response function h(t) represents the response signal for the case where the excitation signal has the form of Dirac's delta function. Under one embodiment, the continuous case is defined by the equation of the form:

$$\delta(t) = \begin{cases} \infty & t = 0 \\ 0 & t \neq 0 \end{cases} \qquad \text{EQ. 1}$$

$$\int_{-\infty}^{\infty} \delta(t)\,dt = 1$$

and in the time-discrete case is defined by the equation of the form:

$$\delta(t) = \begin{cases} 1 & t = 0 \\ 0 & t = \pm 1, \pm 2, \ldots \end{cases} \qquad \text{EQ. 2}$$

In the time-continuous case, the correlation for a linear, time-invariant system is described by the equation of the form:

$$y(t) = \int_0^\infty h(t')u(t-t')dt' \qquad \text{EQ. 3}$$

wherein u(t) represents the input signal or excitation signal, h(t) represents the impulse response function, and y(t) represents the output signal or response signal. In the time-discrete case, the last expression is approximated by the following sum:

$$y(t) = \sum_{t'=0}^{\infty} h(t')u(t-t') \qquad \text{EQ. 4}$$

wherein t and t' take only integer values, as the time interval between successive measurements (sampling interval) is set to 1 without loss of generality. The approximation is improved the smaller the sampling interval or the higher the sampling rate.

As is generally known, the impulse response function contains all frequencies and describes the complete dynamic behavior of the substance that is exposed to the excitation. The desired characteristic quantities of the substance can be derived from the impulse response function. Thus, the frequency response is obtained through a Fourier transformation of the impulse response function. Applied to the field of thermal analysis, the impulse response function can represent, e.g., the heat flow signal after an impulse in the heating rate; i.e., after a temperature jump. In this case, the integral of the impulse response function yields the heat capacity, and its Fourier transform indicates how the heat capacity changes as a function of the frequency. Therefore, it is possible to use the mathematical model to enter excitations that are, to a large extent, freely selectable without actually applying the excitation to the substance and measuring its response, and to determine the properties of the substance from the response of the model. For example, by entering a Dirac impulse, which cannot be physically realized, one directly obtains the impulse response, and the integral of the Dirac impulse delivers the heat capacity.

If the embodiment discussed above is to be applied to a system in which the correlation between the excitation signal and the response signal includes a non-linear portion that is, or is deemed to be, non-negligible, a first solution is to subtract all parts that are associated with the non-linearity from the excitation signal and/or from the response signal and to subject only the resultant amounts of the differences between the signals to the evaluation by means of the linear time-invariant model. However, as a prerequisite for using this procedure, the non-linear parts need to be known or there must be some way to determine them.

However, under a second, alternative solution, the time-invariant, linear model is expanded by adding a mathematical term that takes into account a non-linear portion of the response signal. The defining quantities of this mathematical expression can be determined together with the impulse response function from the time series of the excitation signal and measured values of the response signal. Under one embodiment, the relationship between the excitation signal and the response signal in the kind of system that contains a nonlinearity can be described by an equation of the form:

$$y_s(t) = X + y(t) \qquad \text{EQ. 5}$$

wherein $$y(t) = \int_0^\infty h(t-t')u(t')dt'$$

This alternative solution is of interest primarily in the frequently occurring situation where the non-linear portion X(t) of the response signal y(t) is only slowly variable in comparison to the linear portion y(t). This is the case, e.g., in a dynamic thermal analysis. The heat flow represented by the response signal is, in this case, composed of a reversible heat flow which follows rapid changes of the excitation signal that represents the heating rate, and of an irreversible heat flow which is dictated by thermal events in the substance (e.g., phase transitions or chemical reactions). Because thermal events, as a rule, require a certain amount of time, the heat flow associated with them cannot follow the rapid changes of the excitation signal and thus exhibits a relatively slow variation.

Under the conditions just discussed, the duration of the time series of measured values used for the evaluation can therefore be limited to a time window that is short enough so that the nonlinear portion X(t) during the time window manifests itself as a constant, i.e., so that one can assume:

$$X = c \qquad \text{EQ. 6}$$

during the respective time window. If a significant change occurs within the time window, one can select a linear relationship instead of a constant, i.e., $$X(t) = c_0 + c_1 \cdot (t - t_0), \qquad \text{EQ. 7}$$

wherein $t_0$ represents a freely selectable constant. As a practical matter, $t_0$ is selected as the point in time that lies in the middle of the time window being used in the respective case. In the event this assumed linear form of relationship is inadequate for the required level of accuracy, one can analogously expand the assumed relationship X(t) to also include quadratic or even higher-order terms, or other functions. In this manner, the linear or reversible portion as well as the nonlinear or irreversible portion of the response signal are determined separately.

The assumed relationship expressed in equations 3 and 4 to describe the linear time-invariant system can be used directly as a basis for the mathematical model and, through the known technique of a z-transformation, represented in the form $$y(z) = H(z)u(z), \qquad \text{EQ. 8}$$

wherein y(z), H(z) and u(z) represent the z-transforms of y(t), h(t) and u(t). The model, when subjected to u(t), delivers the estimated value P(t).

In this context, a particularly advantageous embodiment of the inventive method is distinguished by the fact that the z-transformed impulse response function is assumed as a rational function. This means that H(z) takes on the form $$H(z) = \frac{B(z)}{A(z)}, \qquad \text{EQ. 9}$$

wherein B(z) and A(z) represent polynomials of the respective orders $n_b$ and n, of the variable z. It has been found that this assumed rational expression for H(z) describes many practical cases exactly or with adequate approximation. This is a parametric description of the model, wherein the parameters are determined by the coefficients of the denominator polynomial A(z) and the numerator polynomial B(z). By substituting the expression of equation 9 in equation 8, one obtains:

$$A(z)y(z)=B(z)u(z) \qquad \text{EQ. 10}$$

The embodiment represented by equation 10 is also applicable in the case where the excitation consists of more than one value, i.e., contains more than one excitation quantity, or where the response consists of more than one signal, i.e., contains more than one response quantity. In this case, A(z) is a matrix which for each signal contains the coefficients of the associated denominator polynomial. B(z) is a matrix which for each excitation value contains the coefficients of the associated numerator polynomial. Those skilled in the art will not find it unduly difficult to apply the foregoing equations to systems that involve a plurality of different quantities. Guiding comments may be found in textbooks; for example, in MatLab User Manual: System Identification Toolbox User's Guide; The Mathwork, Inc. —Nov. 2000, 4th printing for version 5.0 (Release 12), pages 3-37 to 3-39. One principle of the method is explained below in more detail through an example with one excitation quantity and one response signal quantity, but this should not be interpreted as a limitation. The method may expressly include excitations with more than one excitation quantity and/or responses with more than one response quantity.

As a practical way of determining the impulse response function, the scope of at least one embodiment of the invention includes the concept that the order n, of the denominator polynomial and the order nb of the numerator polynomial of the z-transformed impulse response function are given as fixed numbers and the coefficients of the polynomials are determined so that the relationship between the excitation signal and the response signal as described by the model matches the time series of the measurement values as closely as possible.

As a practical way to carry out the foregoing concept, the relationship between the excitation signal and the response signal as described by the z-transformed impulse response function is represented in the time domain. In the system of linear equations thereby obtained, a sufficient time series of measurement values is inserted so that the equations can be solved for the polynomial coefficients as unknowns.

The representation in the time domain may be obtained by using the shift operator q which, when applied to the z-transformed impulse response function at the discrete time $t_k$, provides the value for the function at the preceding discrete sampling time $t_k-1$ or, expressed in mathematical terms $$q\,h(t_k)=h(t_{k-1})$$

$$q^n h(t_k)=h(t_{k-n}) \qquad \text{EQ. 11}$$

By using the shift operator q of equation 11, equation 10 is transposed into the time domain with the result $$y_k = -a_1 \cdot y_{k-1} - a_2 \cdot y_{k-2} - \ldots - a_{na} \cdot y_{k-na} + \qquad \text{EQ. 12}$$
$$b_1 \cdot u_{k-1} + b_2 \cdot u_{k-2} + \ldots + b_{k-nb} \cdot U_{k-nb} + \varepsilon_k,$$

wherein the indices k, k-1, ... represent the discrete values of the sampling time points, $a_1, a_2, \ldots, a_{na}$ represent the coefficients of the denominator polynomial in equation 9, and $b_1, b_2, \ldots, b_{nb}$ represent the coefficients of the numerator polynomial in equation 9. Without loss of generality, it is assumed that $a_0=1$ in equation 12. Furthermore, the coefficient $b_0$ is assumed to be zero, which is usually the case in real systems because, in practice, the excitation signal does not have an instantaneous effect on the response signal. However, it should be noted that a non-zero value for $b_0$ could be included in the foregoing equation 12 without requiring a change in the procedure described below.

Finally, an error term $\epsilon_k$ has been added on the right-hand side of equation 12, which represents the amount by which the model deviates from the actually measured process.

If the measurement values of the excitation signal and the response signal that occur in equation 12 are combined into a measurement vector $\phi_k$ defined as $$\phi_k=[-y_{k-1},-y_{k-2},\ldots-y_{k-na},u_{k-1},u_{k-2},\ldots u_{k-nb}] \qquad \text{EQ. 13}$$

and the parameter values representing the unknowns are combined into a parameter vector $\Theta$ defined as:

$$\Theta=[a_1,a_2,\ldots a_{na},b_1,b_2,\ldots,b_{nb}]^T \qquad \text{EQ. 14}$$

Equation 12 can be written in matrix format as follows:

$$y_k=\phi_k\cdot\Theta+\epsilon_k \qquad \text{EQ. 15}$$

Thus, $n_a+n_b$ equations are necessary for a complete determination of the parameter vector $\Theta$ which, in turn, requires a time series of a sufficient number of sampling points k, k-1, ... k-n.

The system of equations is solved in such a way that the equation gap $t_k$ is minimized. This can be achieved, e.g., by using the least-square method.

As explained above, when a non-linear portion is added, the right-hand side of equation 12 is extended by an additional term which is obtained by applying the operator polynomial A(q) to the expressions that are defined in equations 6 and 7. This means that the parameter vector $\Theta$ needs to be expanded by corresponding parameters which will likewise be calculated in solving the system of equations. The vector $\phi_k$ is to be expanded in an analogous way.

For example, under one embodiment, if one uses equation 7, $\phi_k$ and $\Theta$ can be expressed as:

$$\phi_k=[1,t,-y_{k-1},-y_{k-2},\ldots-y_{k-na},u_{k-1},u_{k-2},\ldots,u_{k-nb}] \qquad \text{EQ. 16}$$

and $$\Theta=[\gamma_1,\gamma_2,a_1,a_2,\ldots a_{na},b_1,b_2,\ldots,b_{nb}]^T, \text{wherein}$$
$$\gamma_1=c_0\cdot(1+a_1+\ldots+a_p)-c_1\cdot(a_1+2a_2+\ldots+pa_p), \qquad \text{EQ. 17}$$

$$\gamma_2=c_1\cdot(1+a_1+\ldots+a_p). \qquad \text{EQ. 18}$$

In this case, too, equation 15 is applicable, with the vector $y_k$ being composed of the values $y_s(t)$ in equation 5.

The invention has a particularly important application in the known area of dynamic thermal analysis methods. In the excitation signal of these processes, there is often a periodically or non-periodically variable component $u_t$ superimposed on a constant heating rate $\beta_u$, so that the overall heating rate, i.e., the time derivative of the temperature, is given by $$\frac{dT}{dt}=\beta_u+u_t(t) \qquad \text{EQ. 19}$$

In an important class among these procedures, the response signal represents a heat flow of a dynamic thermoanalytical process.

The heat flow occurring in response to the excitation signal represented by the foregoing expression contains a reversible linear portion y(t) which follows the variable portion u(t) of the heating rate, and a non-reversible portion which can substantially be described as a linear function of time, so that one arrives overall at the following representation:

$$\frac{dQ}{dt} = \alpha_0 + \alpha_1 t + y(t) \qquad \text{EQ. 20}$$

In this case, the system of equations discussed above takes the form $$y_k = \gamma_1 + \gamma_2 \cdot t_k - a_1 y_{k-1} - a_2 \cdot y_{k-2} \ldots - \qquad \text{EQ. 21}$$
$$a_{na} \cdot y_{k-na} + b_1 \cdot u_{k-1} + b_2 \cdot u_{k-2} \ldots + b_{k-nb} \cdot u_{k-nb}$$

$$\Theta = [\gamma_1, \gamma_2, a_1, a_2, \ldots a_{na}, b_1, b_2, \ldots, b_{nb}]^T$$

$$\alpha_1 = \frac{\gamma_2}{1 + \sum_{i=1}^{na} a_i}$$

$$\alpha_0 = \frac{\gamma_1 + \alpha_1 \cdot \left(\sum_{i=1}^{na} i \cdot a_i\right)}{1 + \sum_{i=1}^{na} a_i}$$

In the foregoing equations, the parameters $a_1, a_2, \ldots, a_{na}, b_a, b_2, \ldots, b_{nb}$ determine the reversible portion, and the parameters $\gamma_1, \gamma_2$ determine the non-reversible portion. Based on the reversible portion of the heat flow, one can subsequently determine the specific heat capacity according to the known calculation method.

Heat flows can be measured by determining a temperature difference that occurs along the heat flow path. However, one must take into account that, besides the portion contributed by the test substance, there are other contributions to the heat flow that are caused by the calorimetric system used to perform the thermal analysis process. The evaluation of the measurements according to the inventive method yields the total heat flow including its system-related contributions. However, according to the invention, the evaluation can also be applied to processes in which the heat flow is constituted by a difference between respective heat flows to a substance sample and to a known reference substance. The system-related contribution is smaller in these differential methods.

The method according to the invention can also be used to good advantage in the case where the sample corresponds to an inert reference sample, or in the case where the excitation is applied to the system without a sample in place. The method will in this case yield the apparatus properties.

The method according to the invention can further be applied advantageously in the case where the response signal represents a temperature difference of a known dynamic thermoanalysis process (ETA).

Furthermore, the inventive method can be used advantageously in the case where the response signal represents a heating power difference of a dynamic power-compensating thermoanalysis process. Under the power-compensating method, the sample of the test substance and a known reference substance are excited with different levels of heating power in such a manner that the temperature difference between the sample and the reference is constantly regulated to zero. The response to be evaluated in this case consists of the difference in power absorption of the sample in comparison to the reference.

According to the invention, the method can further be used advantageously in the case where the response signal represents a change in length in a dynamic thermo-mechanical analysis process. In a sample that is capable of shrinking, the temperature program representing the excitation signal can cause a simultaneous thermal expansion of the sample and a superimposed shrinkage. According to the invention, the method allows a simultaneous determination of the thermal expansion behavior as reversible portion and the shrinkage behavior as non-reversible portion.

It should be generally noted that the excitation can be known at the outset, so that the excitation values need not be measured. However, this is not a prerequisite for the invention. The invention is also applicable in the event the excitation is unknown and the excitation values are determined by a measurement. In the latter case, an apparatus that is suitable for performing the method needs to be equipped with a measuring device that serves to measure the excitation values. In any event, in a preferred embodiment of the invention, a largely arbitrary excitation can be applied to the mathematical model alone after the parameters have been determined.

BRIEF DESCRIPTION OF THE DRAWINGS

In the following description, the invention will be discussed in more detail with references to the drawing, wherein.

DETAILED DESCRIPTION OF THE DRAWINGS

In the following detailed description, reference is made to the accompanying drawings which form a part hereof wherein like numerals designate like parts throughout, and in which are shown, by way of illustration, specific embodiments in which the invention may be practiced. It is to be understood that other embodiments may be utilized and structural or logical changes may be made without departing from the scope of the present invention. Therefore, the following detailed description is not to be taken in a limiting sense, and the scope of at least one embodiment of the present invention is defined by the appended claims and their equivalents.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification do not necessarily all refer to the same embodiment, but it may. The phrase "A/B" means "A or B". The phrase "A and/or B" means "(A), (B), or (A and B)". The phrase "at least one of A, B and C" means "(A), (B), (C), (A and B), (A and C), (B and C) or (A, B and C)". The phrase "(A) B" means "(A B) or (B)", that is "A" is optional.

Figure 1:
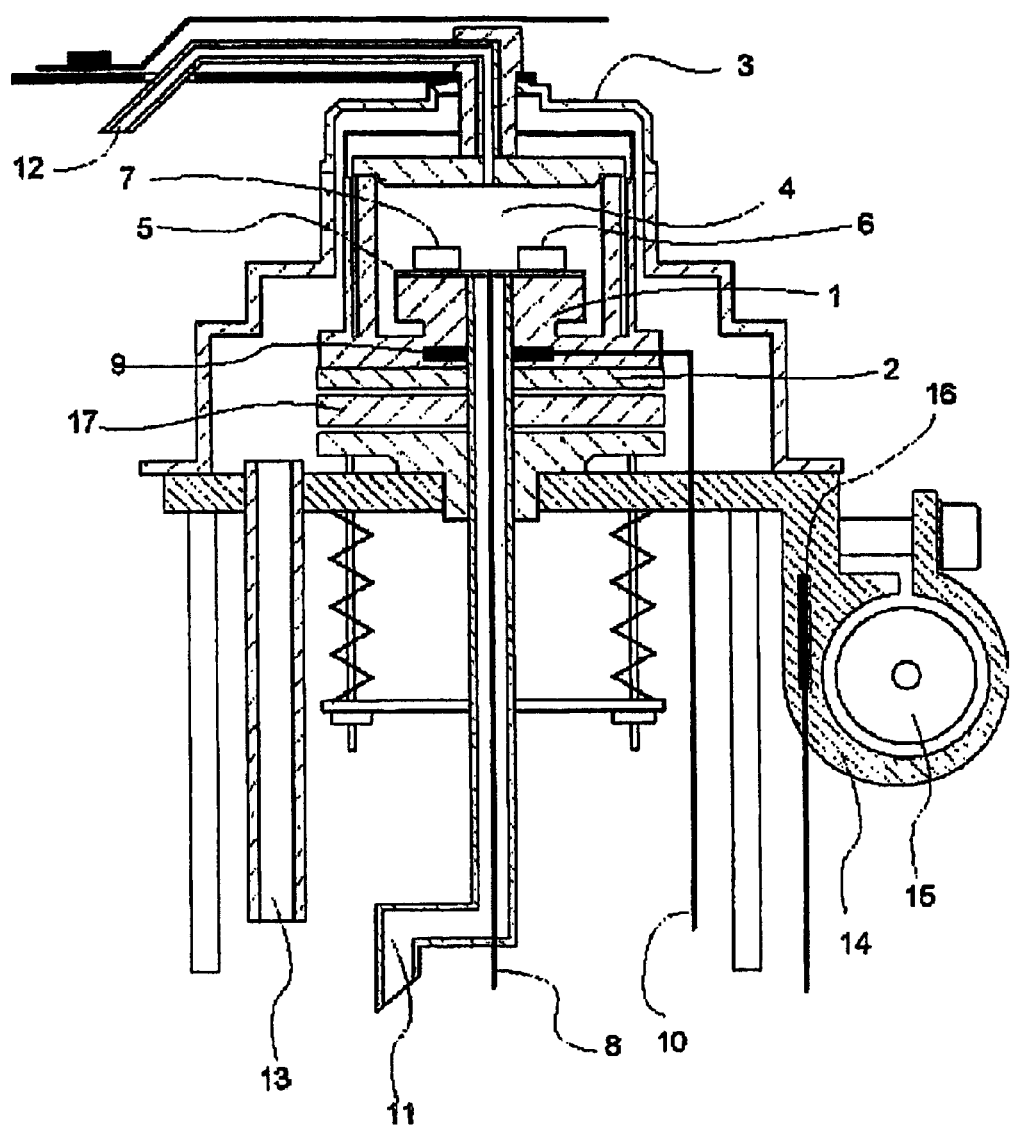
FIG. 1 represents a schematic illustration of a differential calorimeter that is suitable for executing a practical example of the inventive method.

A differential calorimeter as illustrated in a vertical cross-section in FIG. 1 has a hollow cylindrical furnace block 1 which is made of silver and is heatable by a flat resistance heater 2. At its top end, the furnace block 1 is closed off by a lid arrangement 3 which can be taken off to allow access to the interior space 4 of the furnace block 1 for the purpose of loading the furnace.

A disk-shaped substrate 5 extends in the interior space 4 of the furnace block 1 and is thermally coupled to the latter.

On its top surface which extends horizontally in a radial plane, the disk-shaped substrate 5 has one position to receive a sample crucible 6 and, in a thermally symmetric arrangement, a second position to receive a reference crucible 7. The respective positions for the sample crucible 6 and the reference crucible 7 are each equipped with a thermoelement arrangement. In the illustrated embodiment, two electrically opposite ends of the two thermoelement arrangements are connected on the substrate 5, while the two other ends terminate in two signal leads 8 that extend to the outside of the furnace block 1 and are indicated only in a schematic manner. This arrangement results in the thermoelectric signal which occurs between the two signal leads 8 corresponding to the temperature difference AT between the sample position and the reference position. This thermoelectric signal correlates in a known manner to the difference between the two heat flows taking place, on the one hand, between the furnace block 1 and the sample crucible 6 and, on the other hand, between the furnace block 1 and the reference crucible 7.

The resistance heater 2 is connected to a controlled power source (not shown in the drawing) which supplies the electrical heating energy. The power is controlled in such a way that the temperature follows a predetermined dynamic temperature profile as a function of time. The temperature profile is registered by means of a platinum thermometer 9 that is arranged in the furnace block 1 and whose output signal is delivered to the outside of the furnace block 1 through a schematically represented signal lead 10. Thus, the signal leads 10 carry a signal that corresponds to the predetermined temperature profile.

The respective reference symbols 11, 12 and 13 identify a purge gas inlet conduit, a purge gas outlet conduit, and a dry gas supply conduit. Furthermore, the reference symbols 14, 15 and 16 identify a known arrangement of, respectively, a cooling flange, a cooling finger, and a platinum thermometer. A heat-resistance barrier 17 is arranged between the cooling arrangement 14, 15 and the resistance heater 2.

In this differential calorimeter, the temperature profile to which a sample in the sample crucible 6 is exposed inside the furnace block 1 represents the excitation. The signal carried by the signal lead 10, which represents the temperature profile, is detected with a sufficiently fast sampling rate and time-differentiated by a processing device, whereby the time differential of the temperature profile, i.e., the heating rate, is obtained. Synchronous to the sampling of the signal on the signal lead 10, the device also registers the temperature-difference signal AT on the signal lead 8 which represents the differential heat flow that occurs in response to the excitation.

Figure 2:
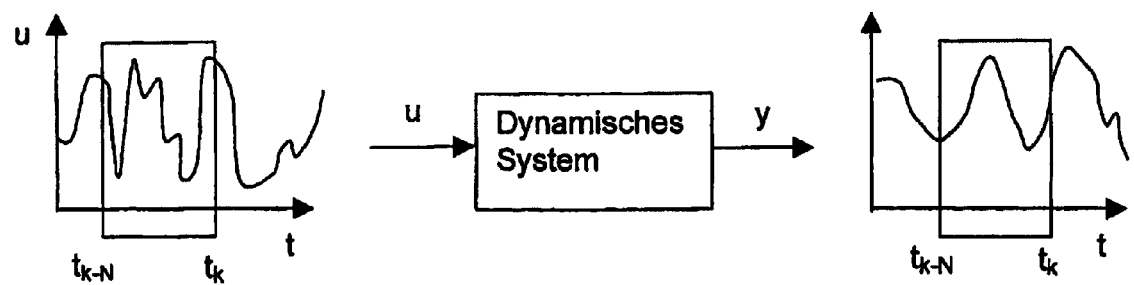
FIG. 2 schematically illustrates the processing of the measurement values that takes place in the practical example of the inventive method.

Through this procedure, one obtains a time series of measurement points of the excitation signal $u(t_k) u(t_{k-1}), \ldots$ that is given by the heating rate as well as a time series of the response signal $y(t_k), y(t_{k-1})$. This is schematically illustrated in FIG. 2. The series of measurement values bracketed between $t_k$ and $t_{k-N}$ in FIG. 2 defines a processing window with a sufficient number of measurement points to allow the solution of the system of equations 15 and 21 discussed hereinabove. This is the case if $N \geq (n_a + n_b)$. Thus, the parameter values of the model are determined anew for every position of the processing window within the entire measured temperature profile. With the parameters determined in this manner, any response of the system can be calculated, in particular its impulse response.

Figure 3:
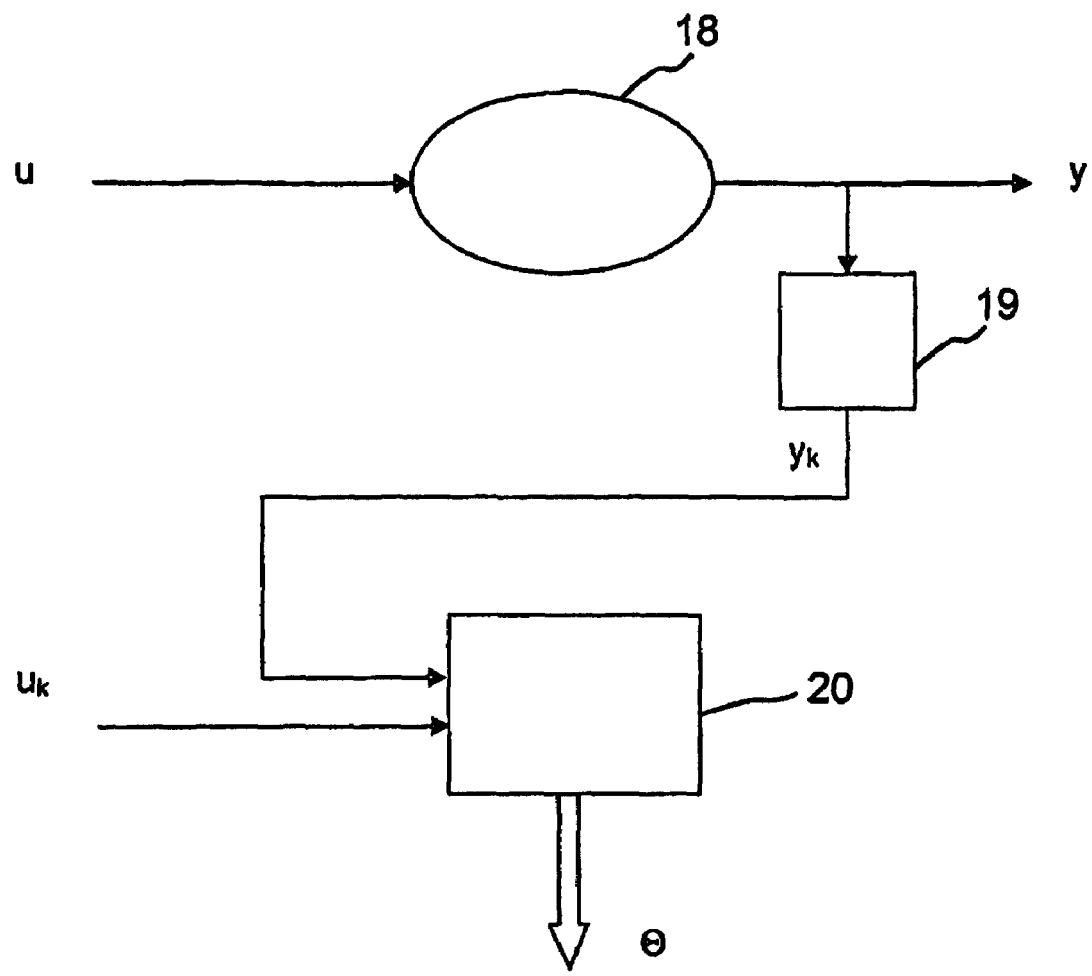
FIG. 3 schematically visualizes the processing steps used to determine the model parameters.
Figure 4:
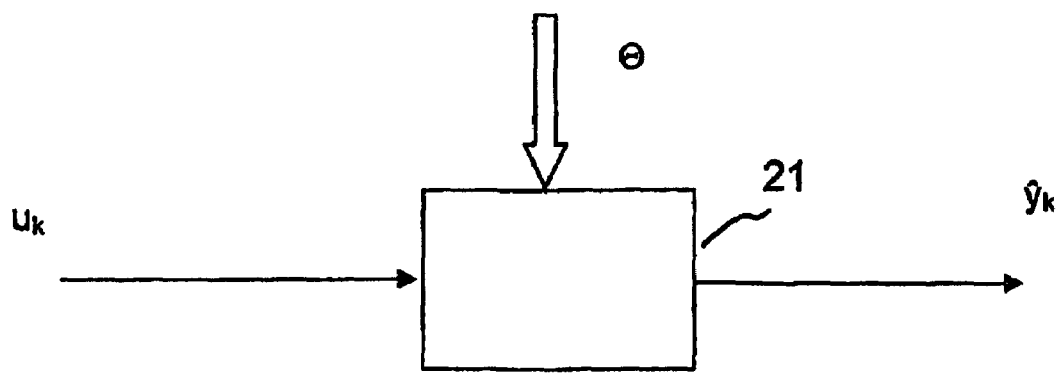
FIG. 4 schematically illustrates how the response values are calculated by the model.

This is illustrated in more detail in FIGS. 3 and 4, where u stands for the excitation signal and y stands for the response signal. The symbol $u_k$ indicates the value of the excitation signal $u(t_k)$ at the sampling time $t_k$, which is either known at the outset or determined by a measurement. Likewise, $y_k$ represents the measurement value of the response signal $y(t_k)$ at the sampling time $t_k$. The symbol $\Theta$ represents the vector of the parameter values as defined hereinabove in equation (14).

With the foregoing definition of symbols, FIG. 3 illustrates the effect of the excitation u on the substance sample 18 and the response y that is returned by the substance sample in reaction thereto. A measuring device 19 samples the response y and delivers the sampling values $y_k$ to a processing device 20 which among other parts includes the mathematical model. The processing device 20 also receives the values $u_k$ of the excitation which in the representation of FIG. 3 are assumed to be known. Based on these input values, the processing device 20 determines the vector $\Theta$ of the parameter values in the manner explained hereinabove with the equations 1 to 21.

FIG. 4 symbolically illustrates how the vector $\Theta$ of the parameter values obtained in accordance with FIG. 3 is entered into the mathematical model 21. Using the values of the vector $\Theta$, the model simulates the relationship between the excitation and the response. As represented in FIG. 4, it is possible with the model to determine estimated response values $\hat{y}k$ for arbitrary values $u_k$ of the excitation and, in turn, to calculate characteristic substance properties from the response values without having to excite the substance and to measure its response.

In the preceding example, the response signal represents the heat flow difference between the sample and the reference. But, in the case of a thermomechanical analysis, the response signal that is registered consists of a change in length of the sample that is exposed to the temperature program.

The processing of the values in accordance with the foregoing discussion is suitable in practice for all signal profiles of the dynamic excitation signal u(t). The excitation signal can, in particular, be a stochastic signal, or a pseudo-stochastic signal in which a stochastic signal sequence of finite duration repeats itself.

The invention claimed is:

1. A method for thermal analysis of substances, comprising:
    exposing a substance to an excitation to cause an observable response;
    providing a mathematical model to describe the relationship between the excitation and the observable response, said mathematical model having a finite number of parameters and being selected to allow derivation of an impulse response function of said substance once said parameters have been determined; and
    evaluating the observable response in accordance with said mathematical model, based on a time series of values of the excitation and measurement values of the observable response, to determine said parameters.

2. The method according to claim 1, wherein the time series of values of the at least one excitation is arbitrarily prescribed.

3. The method according to claim 1, wherein the evaluating includes calculating frequency-dependency of characteristic substance properties.

4. The method according to claim 1, wherein the parameters for a time interval that encompasses at least the time series of the values of the at least one excitation are assumed to be constant over time.

5. The method according to claim 1, wherein the evaluating further comprises determining the parameters for different time intervals separately by means of respective time series that are selected within each of the time intervals.

6. The method according to claim 1, wherein the mathematical model includes a portion that is assumed to be time-invariant and linear.

7. The method according to claim 6, wherein the time-invariant linear portion of the mathematical model is supplemented by a mathematical expression that serves to account for a non-linear part of the response.

8. The method according to claim 6, wherein the time-invariant and linear portion of the mathematical model in a z transformed domain is assumed to be a rational function.

9. The method according to claim 8, wherein an order $n_a$ of a denominator polynomial and a order $n_b$ of a numerator polynomial of the time-invariant and linear portion of the mathematical model are prescribed in the z-transformed domain and coefficients of said denominator and numerator polynomials are determined in such a manner that the relationship between the excitation and the response as described by the mathematical model is in optimal conformance with a time series of the measurement values.

10. The method according to claim 9, wherein the relationship between the excitation and the response described in the z-transformed domain is represented in the time-based domain in accordance with a system of linear equations having polynomial coefficients, the system of equations being configured to be solved for the polynomial coefficients upon insertion of a time series of a sufficient number of values of the at least one excitation and measurement values of the at least one response into said system of equations.

11. The method according to claim 10, wherein the system of equations are selectively solved to minimize an equation gap.

12. The method according to claim 1, wherein the excitation comprises an excitation quantity corresponding to at least a selected one of a variable temperature, a variable amount of power, a variable amount of pressure, a variable amount of radiation, a variable amount of stress or strain, a variable gas atmosphere, and a variable magnetic field.

13. The method according to claim 1, wherein the observable response comprises a response quantity corresponding to at least a selected one of temperature difference and a heat flow of a dynamic thermoanalysis process.

14. The method according to claim 13, wherein the heat flow constitutes a difference between respective heat flows to a sample of the substance and to a known reference substance.

15. The method according to claim 1, wherein the observable response comprises a response quantity corresponding to a heating-power difference of a dynamic power-compensating thermoanalysis process.

16. The method according to claim 1, wherein the observable response comprises a response quantity corresponding to a change in length occurring in a dynamic thermo-mechanical analysis process.

17. The method according to claim 1, wherein the observable response comprises a response quantity that corresponds to a change in weight occurring in a dynamic thermo-gravimetric analysis process.

18. The method according to claim 1, wherein the observable response comprises a response quantity corresponding to a selected one of force and/or a change in length occurring in a dynamic mechanical analysis process.

19. The method according to claim 1, wherein the observable response comprises a response quantity corresponding to a change in voltage occurring in a dynamic dielectric analysis process.

20. The method according to claim 1, further comprising generating the excitation in the absence of a substance to be investigated and determining characteristic quantities of an apparatus from the resulting model.

21. An apparatus comprising:
an excitation device to subject a sample of a substance to a dynamic excitation to cause an observable response;
a measuring device to determine measurement values corresponding to the observable response;
an evaluation device to evaluate the response from a time series of values of the excitation and of associated values of the observable response; and
a calculating device configured in accordance with a mathematical model describing the relationship between the excitation and the observable response; said mathematical model having a finite number of parameters and allowing said parameters to be calculated on the basis of the mathematical model from the time series of values of the excitation and of measurement values of the observable response; the mathematical model being selected so as to allow to therefrom derive the impulse response function of said substance once said parameters have been calculated.

22. The apparatus according to claim 21, wherein the excitation device comprises a profile device to generate a temperature profile as a function of time and further comprises a coupling device to establish a thermal coupling of the sample, wherein the measuring device serves to measure a heat flow that is influenced by the sample.

23. The apparatus according to claim 22, wherein the coupling device establishes a symmetrical thermal coupling of a reference material and the measurement device measures the difference between the heat flow to the sample and the heat flow to the reference material.

24. The apparatus according to claim 21, wherein the excitation device comprises a profile device to generate a temperature profile as a function of time, a coupling device to establish a thermal coupling of the sample and a reference material, and also a regulation device to regulate a temperature difference between the sample and the reference material to maintain said difference at about zero; and wherein the measuring device measures the difference between the respective amounts of heating power supplied to the sample and to the reference material, said difference in the respective amounts of heating power to regulate a zero temperature difference.

25. The apparatus according to claim 21, wherein the excitation device comprises a profile device to generate a temperature profile as a function of time and a coupling device to establish a thermal coupling of the sample; and the measuring device is configured to measure a change in length of the sample.

26. The apparatus according to claim 21, wherein a device delivering the values of the excitation signal is provided for the measurement of an excitation signal representing the excitation.

27. A method for thermal analysis of substances, comprising:
exposing a substance to an excitation to cause an observable response, said excitation corresponding to a variable temperature and said observable response corresponding to a selected one of a heat flow of a dynamic thermoanalysis process and a heating-power difference of a dynamic power-compensating thermoanalysis process;

providing a mathematical model describing the relationship between the excitation and the observable response; said mathematical model having a finite number of parameters and being selected so as to allow to therefrom derive the impulse response function of said substance once said parameters have been determined;

evaluating the observable response in accordance with said mathematical model in accordance with a time series of values of the excitation and measurement values of the observable response, and by the mathematical model itself to determine said parameters; and determining a heat capacity of said substance as an integral of said impulse response function.

* * * * *